United States Patent

Alfano et al.

[11] Patent Number: 6,151,522
[45] Date of Patent: Nov. 21, 2000

[54] METHOD AND SYSTEM FOR EXAMINING BIOLOGICAL MATERIALS USING LOW POWER CW EXCITATION RAMAN SPECTROSCOPY

[75] Inventors: Robert R. Alfano, Bronx; Wubao Wang, Flushing, both of N.Y.

[73] Assignee: The Research Foundation of CUNY, New York, N.Y.

[21] Appl. No.: 09/270,383

[22] Filed: Mar. 16, 1999

Related U.S. Application Data

[60] Provisional application No. 60/078,134, Mar. 16, 1998.

[51] Int. Cl.$^7$ .................................. A61B 6/00; G01J 3/44
[52] U.S. Cl. ........................ 600/473; 600/310; 600/475; 356/301; 356/303
[58] Field of Search .................................... 600/473, 475, 600/476, 477, 310, 316, 318, 319; 356/39, 40, 41, 42, 300, 301, 303

[56] References Cited

U.S. PATENT DOCUMENTS

| | | | |
|---|---|---|---|
| 4,193,690 | 3/1980 | Levenson et al. | 356/301 |
| 5,243,983 | 9/1993 | Tarr et al. | 600/318 |
| 5,261,410 | 11/1993 | Alfano et al. | 600/475 |
| 5,293,872 | 3/1994 | Alfano et al. | 600/475 |
| 5,991,653 | 11/1999 | Richards-Kortum et al. | 600/475 |
| 6,044,285 | 3/2000 | Chaiken et al. | 600/316 |

*Primary Examiner*—Sang Paik
*Attorney, Agent, or Firm*—Kriegsman & Kriegsman

[57] ABSTRACT

A method and system for examining biological materials using low-power cw excitation Raman spectroscopy. In accordance with the teachings of the invention, a low-power continuous wave (cw) pump laser beam and a low-power cw Stokes (or anti-Stokes) probe laser beam simultaneously illuminate a biological material and traverse the biological material in collinearity. The pump beam, whose frequency is varied, is used to induce Raman emission from the biological material. The intensity of the probe beam, whose frequency is kept constant, is monitored as it leaves the biological material. When the difference between the pump and probe excitation frequencies is equal to a Raman vibrational mode frequency of the biological material, the weak probe signal becomes amplified by one or more orders of magnitude (typically up to about $10^4$–$10^6$) due to the Raman emission from the pump beam. In this manner, by monitoring the intensity of the probe beam emitted from the biological material as the pump beam is varied in frequency, one can obtain an excitation Raman spectrum for the biological material tested. The present invention may be applied to in the in vivo and/or in vitro diagnosis of diabetes, heart disease, hepatitis, cancers and other diseases by measuring the characteristic excitation Raman lines of blood glucose, cholesterol, serum glutamic oxalacetic transaminase (SGOT)/serum glutamic pyruvic tansaminase (SGPT), tissues and other corresponding Raman-active body constituents, respectively. For example, it may also be used to diagnose diseases associated with the concentration of Raman-active constituents in urine, lymph and saliva It may be used to identify cancer in the breast, cervix, uterus, ovaries and the like by measuring the fingerprint excitation Raman spectra of these tissues. It may also be used to reveal the growing of tumors or cancers by measuring the levels of nitric oxide in tissue.

22 Claims, 17 Drawing Sheets

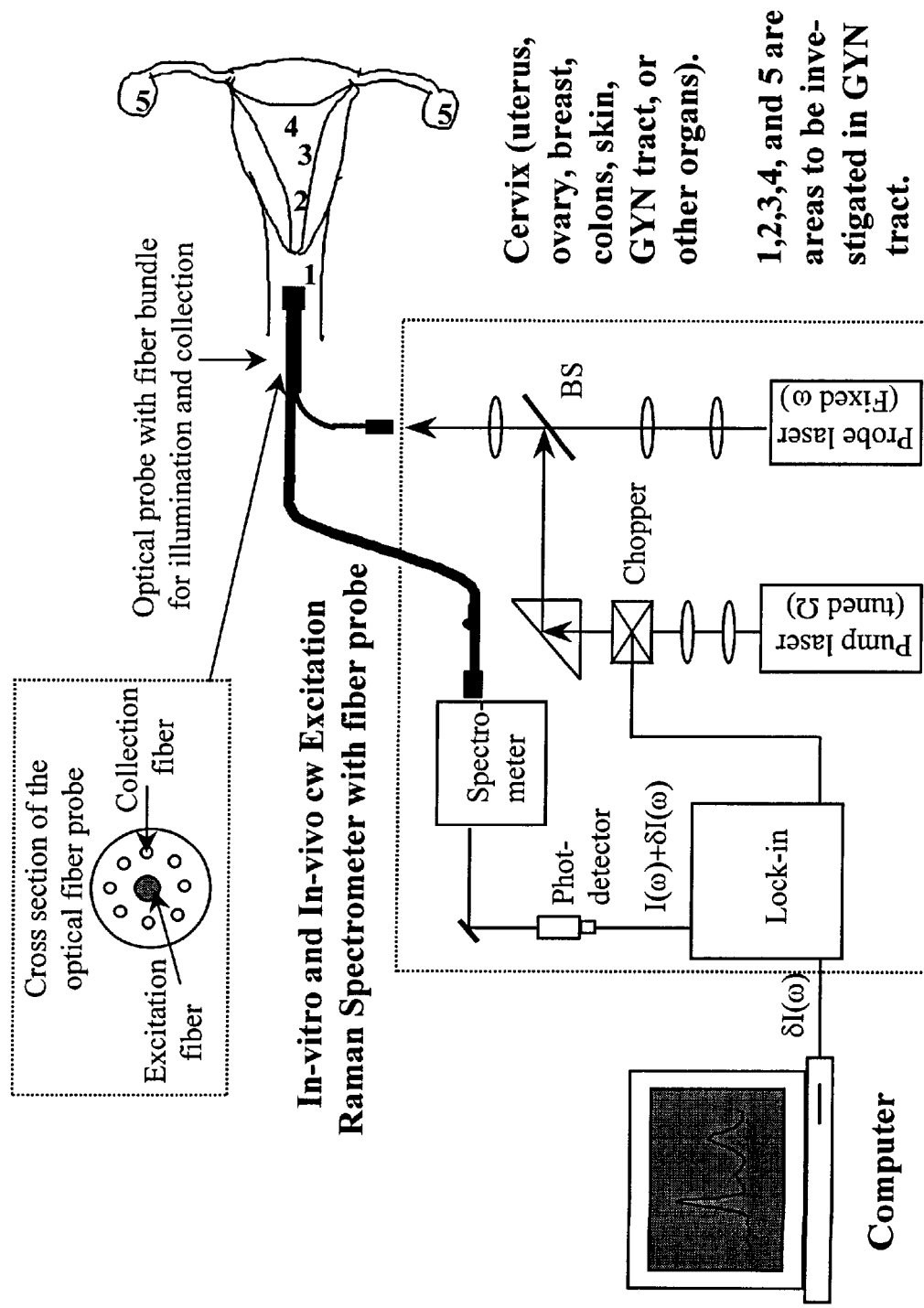

METHOD AND SYSTEM FOR EXAMINING BIOLOGICAL MATERIALS USING LOW POWER CW EXCITATION RAMAN SPECTROSCOPY

CROSS-REFERENCE TO RELATED APPLICATIONS

The present invention claims the benefit under 35 U.S.C. § 119(e) of U.S. Provisional Patent Application Serial No. 60/078,134, filed Mar. 16, 1998, the disclosure of which is incorporated herein by reference.

BACKGROUND OF THE INVENTION

The present invention relates generally to methods and systems for examining biological materials and more particularly to methods and systems for examining biological materials using Raman spectroscopy.

A variety of Raman spectroscopic techniques have been reported in the art as being either useful or potentially useful in medical applications. For example, in U.S. Pat. No. 5,261,410, inventors Alfano et al., which issued Nov. 16, 1993, and which is incorporated herein by reference, there is disclosed a method for determining if a tissue is a malignant tumor tissue, a benign tumor tissue, or a normal or benign tissue using Raman spectroscopy. The method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445 and 1651 $cm^{-1}$ for normal or benign tissue, the presence of three Raman bands at a Raman shift of about 1240, 1445 and 1659 $cm^{-1}$ for benign tumor tissue, and the presence of two Raman bands at a Raman shift of about 1445 and 1651 $cm^{-1}$ for malignant tumor tissue. In addition, it was discovered that, for human breast tissue, the ratio of intensities of the Raman bands at a Raman shift of about 1445 and 1650 $cm^{-1}$ is about 1.25 for normal or benign tissue, about 0.93 for benign tumor tissue, and about 0.87 for malignant tumor tissue.

As another example, in U.S. Pat. No. 5,293,872, inventors Alfano et al., which issued Mar. 15, 1994, and which is incorporated herein by reference, there is disclosed a method for distinguishing between, on one hand, calcified atherosclerotic tissue and, on the other hand, fibrous atherosclerotic tissue or normal cardiovascular tissue using Raman spectroscopy. The method is based on the discovery that, when irradiated with a beam of monochromatic infrared light, calcified atherosclerotic human aortic tissue produces a Fourier Transform Raman spectrum which is distinguishable from analogous spectra obtained from fibrous atherosclerotic human aortic tissue and normal human aortic tissue. Some salient differences in the respective Raman spectra are the presence of five Raman bands at Raman shifts of 957, 1071, 1262–1300, 1445, and 1659 $cm^{-1}$ ($\pm 4$ $cm^{-2}$ for all shifts) for the calcified tissue as compared to three Raman bands at Raman shifts of 1247–1270, 1453 and 1659 $cm^{-1}$ ($\pm 4$ $cm^{-1}$ for all shifts) for the fibrous tissue and three Raman bands at Raman shifts of 1247–1270, 1449 and 1651 $cm^{-1}$ ($\pm 4$ $cm^{-1}$ for all shifts) for the normal tissue. In addition, it was discovered that the ratios of intensities for the Raman bands at 1659 and 1453 $cm^-$ and at 1254 and 1453 $cm^{-1}$ were 0.69 and 0.53, respectively, for the calcified tissue, 1.02 and 0.85, respectively, for the fibrous tissue and 1.2 and 0.83, respectively, for the normal tissue.

As yet another example, in U.S. Pat. No. 5,243,983, inventors Tarr et al., which issued Sep. 14, 1993, and which is incorporated herein by reference, there is disclosed a non-invasive blood glucose measurement system and method using stimulated Raman spectroscopy. The system and method make use of two monochromatic laser beams, a pump laser beam and a probe laser beam. The output power of the pump laser beam is amplitude modulated, combined with the probe laser beam and directed into the ocular aqueous humor of a living being. The introduction of the laser beams into the ocular aqueous humor induces scattered Raman radiation, which causes a portion of the energy at the pump frequency to shift over to the probe frequency. The pump and probe laser beams are then detected as they exit the ocular aqueous humor. The probe laser beam is filtered, converted into an electrical signal and amplified. It is then compared to the modulation signal to generate an electrical signal representative of the concentration of D-glucose in the ocular aqueous humor.

Some of the problems with Raman spectroscopic techniques of the type described above (e.g., spontaneous Raman spectroscopy, coherent anti-stokes Raman spectroscopy and pulse-pumped stimulated Raman spectroscopy) are that such techniques typically require a long exposure time (i.e., several minutes) and high power laser pump fluency that exceeds the safety limitations for laser illumination in human body applications. As can readily be appreciated, requirements such as these substantially limit the practical applicability of these techniques in the fields of in vivo and in vitro medical diagnostics.

Other documents of interest include Owyoung, "Coherent Raman Gain Spectroscopy Using CW Laser Sources," *IEEE Journal of Quantum Electronics*, QE-14(3):192–202 (1978); Liu et al., "Raman, fluorescence, and time-resolved light scattering as optical diagnostic techniques to separate diseased and normal biomedical media, *J. Photochem. Photobiol. B: Biol.*, 16:187–209 (1992); Lowenstein et al., "Nitric Oxide: A Physiologic Messenger," *Ann Intern Med.*, 120:227–237 (1994); and Berger et al., "Feasibility of measuring blood glucose concentration by near-infrared Raman spectroscopy," *Spectrochimica Acta Part A*, 53:287–292 (1997), all of which are incorporated herein by reference.

SUMMARY OF THE INVENTION

It is an object of the present invention to provide a novel method and system for examining biological materials using Raman spectroscopy.

It is another object of the present invention to provide a method and system as described above that overcome at least some of the problems associated with existing Raman spectroscopic methods and systems for examining biological materials.

It is still another object of the present invention to provide a method and system as described above that may be used in in vivo and/or in vitro medical diagnostics.

In accordance with the above objects, as well as with those objects to become apparent from the description to follow, there is hereinafter disclosed a novel method and system for examining biological materials, said method and system employing a low-power continuous wave (cw) pump laser beam and a low-power cw Stokes (or anti-Stokes) probe laser beam. The pump beam and the probe beam simultaneously illuminate the biological material and traverse the biological material in collinearity. The pump beam, whose frequency is varied, is used to induce Raman emission from the biological material. The intensity of the probe beam, whose frequency is kept constant, is monitored as it leaves the biological material. When the difference between the pump ($\Omega$) and probe ($\omega$) excitation frequencies is equal to a Raman vibrational mode frequency (v) of the biological material, the weak probe signal becomes amplified by one or more orders of magnitude (typically up to about $10^4$–$10^6$) due to the Raman emission from the pump beam. In this manner, by monitoring the intensity of the probe beam emitted from the biological material as the pump beam is varied in frequency, one can obtain an excitation Raman spectrum for the biological material tested.

The present invention may be applied to in the in vivo and/or in vitro diagnosis of diabetes, heart disease, hepatitis, cancers and other diseases by measuring the characteristic excitation Raman lines of blood glucose, cholesterol, serum glutamic oxalacetic tansaminase (SGOT)/serum glutamic pyruvic transaminase (SGPT), tissues and other corresponding Raman-active body constituents, respectively. For example, it may also be used to diagnose diseases associated with the concentration of Raman-active constituents in urine, lymph and saliva. It may be used to identify cancer in the breast, cervix, uterus, ovaries and the like by measuring the fingerprint excitation Raman spectra of these tissues. It may also be used to reveal the growing of tumors or cancers by measuring the levels of nitric oxide in tissue.

Some of the advantages of the present invention are that the subject method can be performed in a short detecting time (i.e., on the order of several seconds as opposed to several minutes) and that the pump and probe beams can be operated at a power of up to four orders of magnitude less than that typically used in pulsed coherent Raman spectroscopic techniques.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts:

FIG. 16 is a schematic diagram of a third embodiment of a system constructed according to the teachings of the present invention for examining biological materials using low-power cw excitation Raman spectroscopy.

DETAILED DESCRIPTION OF PREFERRED EMBODIMENTS

As noted above, the present invention is directed to novel method and system for examining biological materials, said method and system employing a low-power continuous wave (cw) pump laser beam and a low-power cw Stokes (or anti-Stokes) probe laser beam. The pump beam and the probe beam are made to simultaneously illuminate and traverse the biological material in collinearity. The pump beam, whose frequency is varied, is used to induce Raman emission from the biological material. The intensity of the probe beam, whose frequency is kept constant, is monitored as the probe beam is emitted from the biological material. When the difference between the pump ($\Omega$) and probe ($\omega$) excitation frequencies is equal to a Raman vibrational mode frequency (v) of the biological material, the weak probe signal becomes amplified by one or more orders of magnitude (typically up to about $10^4$–$10^6$) due to the Raman emission from the pump beam. In this manner, by monitoring the intensity of the probe beam emitted from the biological material as the pump beam is varied in frequency, one can obtain an excitation Raman spectrum for the biological material tested.

Figure 1A:
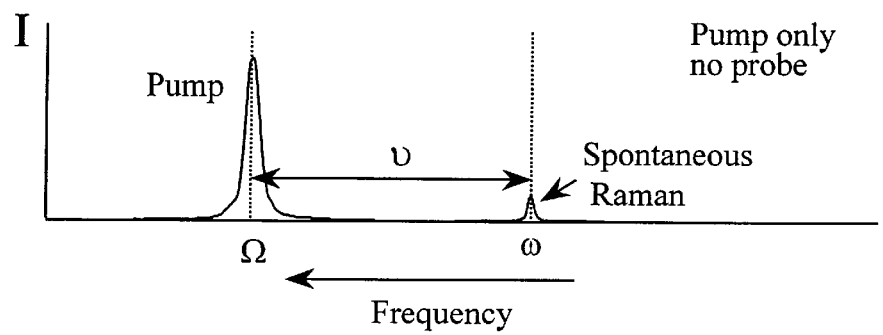
FIGS. 1(a) through 1(e) are graphic representations of signals produced under different conditions for pump and probe beams during Raman gain processes.
Figure 1B:
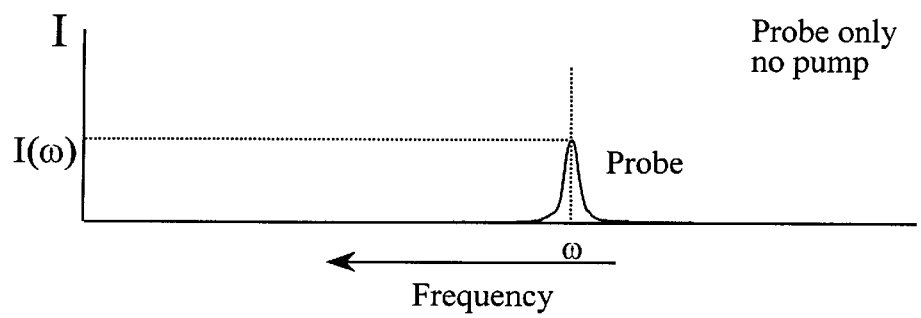
Figure 1C:
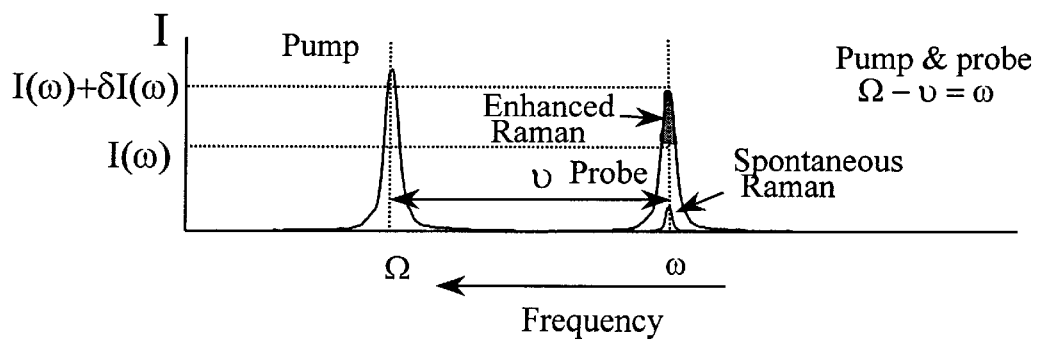
Figure 1D:
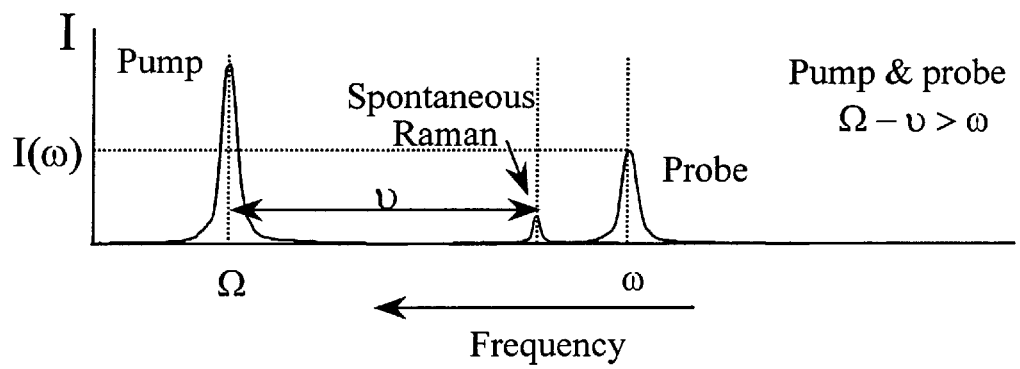
Figure 1E:
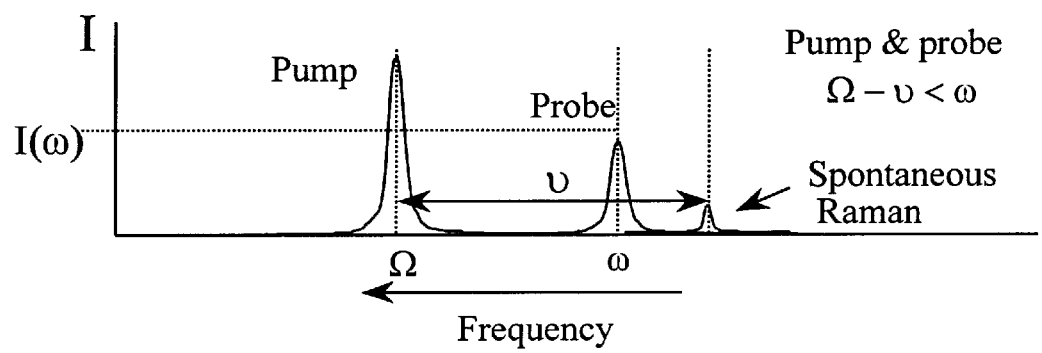

Referring now to FIGS. 1(a) through (b), there is shown a series of drawings which illustrate the principles underlying the present invention. In FIG. 1(a), only a pump beam is used to irradiate the sample, the result being a weak spontaneous Raman signal emitted by the sample in response to the pump beam. In FIG. 1(b), only a probe beam is used to irradiate the sample, the result being a spontaneous Raman signal emitted by the sample in response to the probe beam, said spontaneous Raman signal emitted in response to the probe beam being much weaker than the corresponding spontaneous Raman signal emitted in response to the pump beam in FIG. 1(a) (said spontaneous Raman signal emitted in response to the probe beam not even being shown in FIG. 1(b). In FIG. 1(c), both the pump beam and the probe beam are used to irradiate the sample, the respective frequencies of the two beams, $\Omega$ and $\omega$, being such that the spontaneous Raman signal from the pump is located at the probe frequency. Under these conditions, energy is transferred from the pump beam to the probe beam via Raman gain processes, the result being a gained Raman signal at the probe frequency $\omega$ that is 10 to $10^4$ times larger than the spontaneous Raman signal emitted in response to the pump beam. In FIGS. 1(d) and 1(e), the pump beam frequency is off the resonant condition, $\Omega - v \neq \omega$, resulting in no gain at the probe frequency $\omega$ and only a weak spontaneous Raman signal at $\Omega - v$.

Figure 2A:
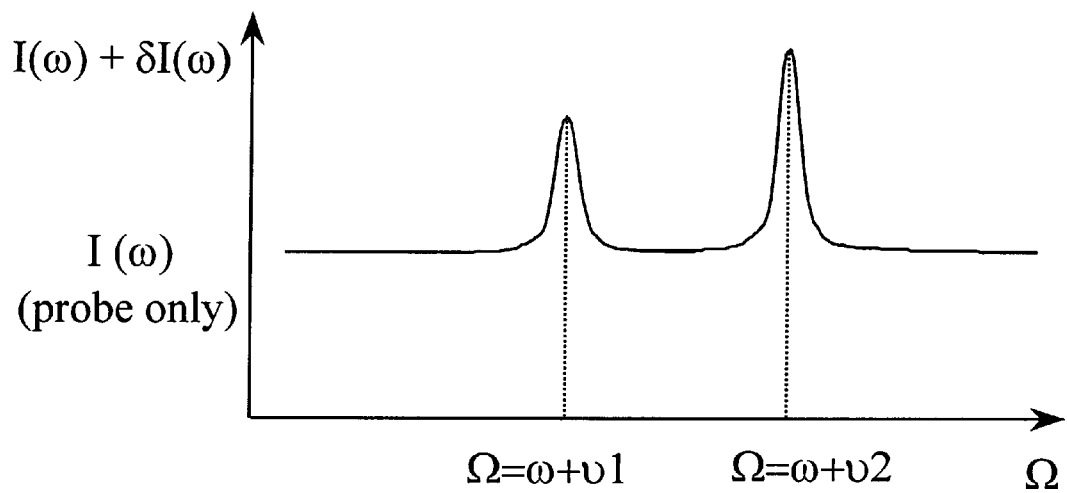
FIGS. 2(a) and 2(b) are graphic representations of total probe signals produced as a function of pump frequency $\Omega$ without and with the use of lock-in detection, respectively.
Figure 2B:
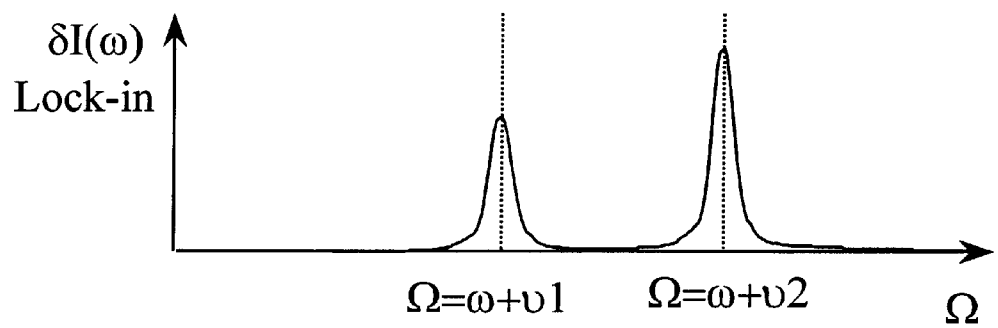

Referring now to FIGS. 2(a) and 2(b), there are shown two excitation Raman spectra obtained in accordance with the principles of the present invention, the two Raman spectra being of the same sample at the same probe wavelength $\omega$ as the pump frequency $\Omega$ is varied over the same bandwidth, the only difference between the two spectra being that the spectrum of FIG. 2(b) is further obtained using a lock-in detection technique. More specifically, as can be seen in FIG. 2(a), there is a large background due to the probe at non-resonant conditions. Consequently, in FIG. 2(b), a standard lock-in detection technique is employed wherein the pump beam is modulated by a chopper at frequency $f_0$. Modulation of the pump beam is thus reflected in the modulated Raman gain at the Stokes (or anti-Stokes) frequency. The use of lock-in detection can, therefore, remove the large background intensity of the probe beam since only the Raman signal at the probe frequency $\omega$ under the resonant condition, $\Omega - v = \omega$, will be enhanced and modulated at the pump's chopping frequency $f_0$ and the probe beam signal at other frequencies ($\Omega - v \neq \omega$) will not be modulated at $f_0$.

Figure 3:
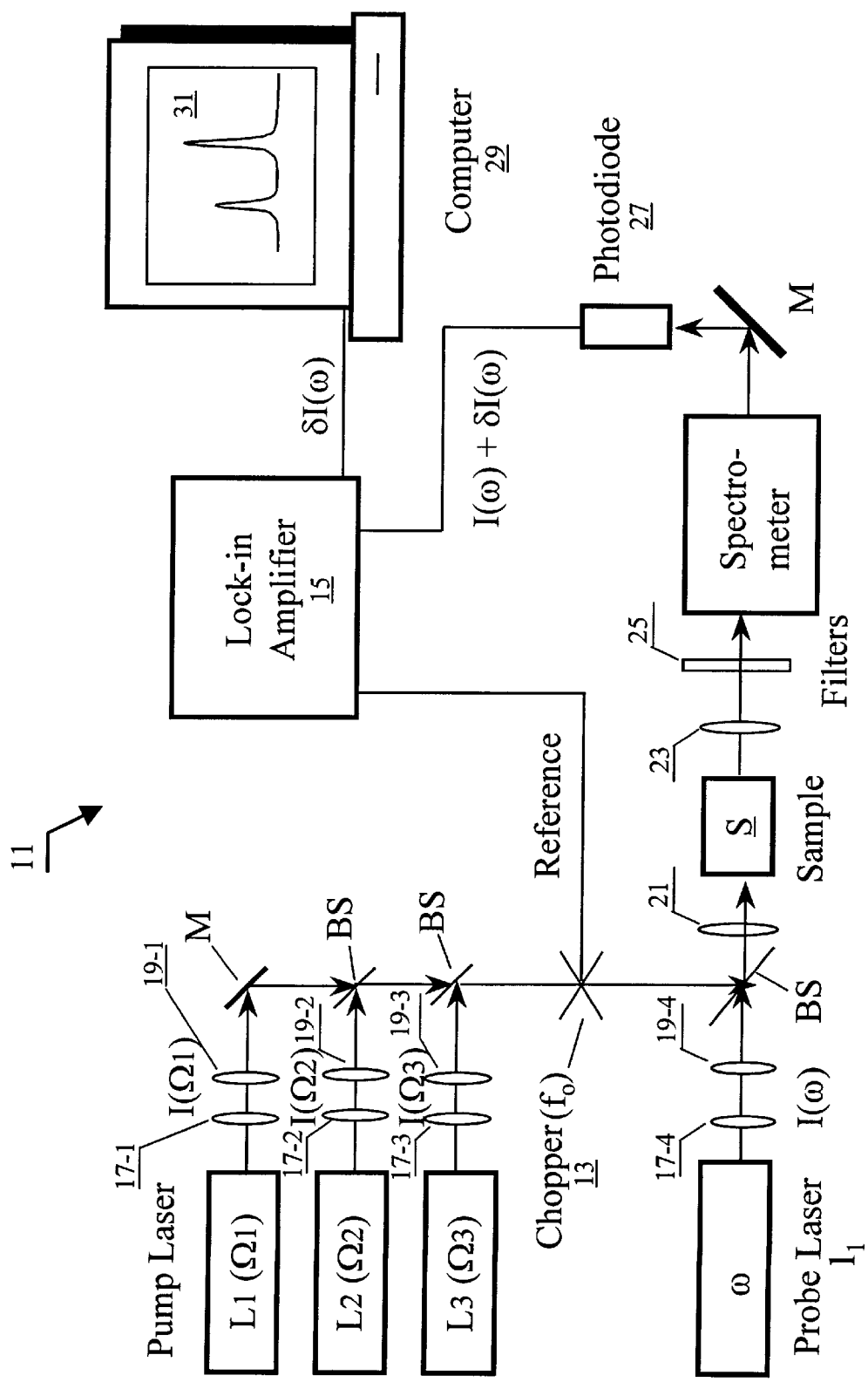
FIG. 3 is a schematic diagram of a first embodiment of a system constructed according to the teachings of the present invention for examining biological materials using low-power cw excitation Raman spectroscopy.

Referring now to FIG. 3, there is shown a schematic diagram of a first embodiment of a system constructed according to the teachings of the present invention for examining biological materials using low-power cw excitation Raman spectroscopy, the system being represented generally by reference numeral 11.

System 11 includes a plurality of pump lasers $L_1$, $L_2$ and $L_3$ emitting at different frequencies $\Omega_1$, $\Omega_2$ and $\Omega_3$, respectively. System 11 also includes a probe laser $l_1$ emitting at still another frequency $\omega$. As an example of suitable probe and pump lasers, a single-mode laser such as a He—Ne laser operating on a single longitudinal mode of 632.8 nm with an output power of ~5 mW could be used as the probe laser, and an array of three semiconductor lasers of different frequencies or a wavelength-tunable dye laser could be used as the pump laser. As another example, the probe and pump lasers could be a 830 nm semiconductor diode laser and a Ti:Sapphire laser, respectively.

System 11 also includes a chopper 13 associated with a lock-in amplifier, the pump beam being passed through chopper 13 modulate the pump beam with a frequency of 30 Hz to a few kHz. System 11 also includes a plurality of lenses 17-1 through 17-4 and 19-1 through 19-4, mirrors M and beam-splitters BS for collimating the respective beams and for giving the beams nearly identical beam diameters. A dichroic beam splitter DBS is used to combine the probe and pump beams and to adjust them for collinearity. The combined probe and pump beams are then focused by a lens 21 onto the biological material sample S. Light emitted by the sample S is then collected by a lens 23 and passed through a filter 25 selective for light at the probe wavelength $\omega$. The filtered light is then detected by a photodiode 27 (or photomultiplier). The modulated signal $\delta I(\omega)$ at the probe wavelength refelects the gain produced by the modulated pump beam. The probe signal detected by photodiode 27 is amplified and demodulated by amplifier 15 and then processed by a computer 29 having a monitor 31. The excitation Raman spectrum is plotted on monitor 31.

Although not wishing to be limited to any particular theory behind the invention, the following describes the excitation Raman gain process: The measured total output signal at the probe frequency $\omega$ including the probe, the spontaneous Raman and the stimulated Raman gain signal induced by a pump beam at frequency $\omega$ can be expressed as:

$$I_{total}(\omega) = [I(\omega) + I_s(\omega) + \sigma I(\Omega)] e^{gl\, I(\Omega)} \quad (1)$$

where $I(\omega)$, $I_s(\omega)$ and $I(\Omega)$ are the probe, spontaneous noise and pump intensities, respectively; $\sigma$ is the Raman cross-section; g is the gain factor of the individual scattering process, and l is the interaction length over which amplification takes place. The term $\sigma I(\Omega)$ is the spontaneous Raman caused by the pump beam. For a small value of gain factor g ($\sim 10^{-9}$ cm/W), the gain $glI(\Omega)$ is small and therefore $e^{gl\,I(\Omega)} \approx 1 + gl\, I(\Omega)$.

The $I_{total}(\omega)$ can also be expressed as:

$$I_{total}(\omega) = I(\omega) + \sigma I(\omega), \quad (2)$$

where $\delta I(\omega)$ is the gain intensity at the probe frequency $\omega$ caused by the pump beam when $\Omega - \sigma = \omega$. Since $I_s(\omega) << I(\omega)$, $\sigma$ and g are small, the single-pass gain $\delta I(\omega)/I(\omega)$ can, by comparing Eqns. (1) and (2), be given by:

$$\delta I(\omega)/I(\omega) = gl\, I(\omega). \quad (3)$$

In our cw excitation Raman spectroscopy measurements, the typical values are: $I(\Omega) \sim 100$ mW/$(10^{-3}$ cm$)^2$, g~$2.5 \times 10^{-9}$ cm/W, the single-pass Raman gain $\delta I(\omega)/I(\omega)$ was calculated to be on the order of $10^{-5}$ for l=0.1 cm, and on the order of $10^{-3}$ for l=1 cm, which can be easily measured using the standard lock-in technique.

For the case of Gaussian pump and probe beams with identical beam parameters, the fractional power gain at the probe frequency $\omega$ induced by a pump beam at frequency $\Omega$ is given approximately by $$\delta P(\omega)/P(\omega) = (384\pi^4/\lambda^2 cn) Im\chi_3^{iiii}(-\omega,\omega, \Omega,-\Omega) P(\Omega), \quad (4)$$

where $P(\omega)$, $P(\Omega)$ and $\delta P(\omega)$ are the probe, pump and gain powers, respectively, n is the refractive index at the probe frequency $\omega$, $\lambda^2$ is given by $(2\pi c)^2 \Omega^{-1} \omega^{-1}$, and $Im\chi_3^{iiii}(-\omega,\omega,\Omega,-\Omega)$ is the imaginary part of the third-order nonlinear susceptibility. When the difference between the pump and probe frequencies ($\Omega-\omega$) is coincident with the Raman mode v of the medium, the nonlinear susceptibility element $\chi_{3i}^{iiii}(-\omega,\omega,\Omega,-\Omega)$ attains a maximum value given by $$\chi_3^{iiii}(-\omega,\omega,\Omega,-\Omega)=(Nc^3/48\hbar\omega^4)[d\sigma/d\Omega d(1/\lambda)]L(\Omega-\omega) \quad (5)$$

where N is the population difference between the Raman levels, $L(\Omega-\omega)$ is the line-shape function which attains its peak value of unity at the mode's line center and is an odd function of $(\Omega-\omega)$, and $d\sigma/d\Omega d(1/\lambda)$ is the peak Raman cross-section given in unit of $cm^2/(sr\ cm^{-1})$. Usually, only a few large gains (g) are observed for the Raman modes which have larger cross-sections and small bandwidths, and therefore, large values of $d\sigma/d\Omega d(1/\lambda)$.

Several advantages of excitation Raman spectroscopy (ERS) over spontaneous Raman spectroscopy (SRS) and coherent anti-stokes Raman spectroscopy (CARS) can immediately be seen from equations (1) through (5).

For example, the measured fractional power gain $\delta P(\omega)/P(\omega)$ for ERS is linearly dependent on the $\chi_3$ and on the pump power $P(\Omega)$ which is in contrast with the quadratic dependence of CARS. Because of this dependence, the ERS technique offers significantly stronger output signal power levels for low-density or low-concentration applications using low-power cw laser sources. In fact, even for strong Raman scattering with $Im\chi_3^{iiii}=15.9\times10^{14}\ cm^3/erg$, a pump power of 100 mW yields an ERS signal $\delta P(\omega)$ that is nearly six orders of magnitude larger than that obtained at comparable power levels in CARS and other Raman methods.

In addition, for a weak Raman signal, the background fluorescence usually precludes the use of SRS whereas, with ERS, the Raman signal is detected at the probe wavelength—which is much stronger than that of the background fluorescence. This is a considerable advantage for weak Raman detection. The exposure time for collecting the Raman signal in the ERS technique is also 10–100 times less than that needed for the SRS technique.

Moreover, since the measured ERS signal is only proportional to the imaginary part of the nonlinear susceptibility, $Im\chi_3$, as shown in Eqn. (4), ERS yields Raman spectra directly with no interference from either background non-linearities or dispersion in $Re\chi_3$.

Additionally, ERS is self-phase-matched and thus requires only a spatial overlap of two beams to incur for an interaction whereas CARS is a parametric mixing process which requires not only a spatial overlap but also a temporal overlap and phase matching for 2 or 3 beams which make the CARS technique much more complex in real applications.

Furthermore, the self-phase-matched interaction of ERS is considerably insensitive to slight polarization within the sample; therefore, optical fiber guides and multiple-pass Raman cells may be used to greatly further enhance the effective optical interaction region and, hence, the sensitivity of the technique.

In addition, the signal to noise ratio in the excitation Raman gain measurement is given by:

$$R=S/N=n(\delta I(\omega))/(n(I(\omega)))^{1/2}. \quad (6)$$

In our experimental conditions, $n(\delta I(\omega))$ was estimated to be $8\times10^{11}$ photons/sec, and $n(I(\omega))$ is estimated to be $3.2\times10^{18}$ photons/sec. The ratio R=S/N is calculated to be as high as $\sim 4.5\times10^3$, which indicates the good accuracy of the detected Raman gain signal.

The technique of the present invention also differs from the technique described in U.S. Pat. No. 5,243,983 ("the '983 patent") in at least the following respects: (1) The technique of the '983 patent relates only to blood glucose measurements taken in the eye whereas the technique of the present invention is not so limited. (2) The technique of the '983 patent utilizes only a narrow portion of the Raman spectrum from 200 $cm^{-1}$ to 1000 $cm^{-1}$ whereas our technique is not so limited. For example, in our technique, we preferably examine the Raman spectrum from 400 $cm^{-1}$ to 1800 $cm^{-1}$ for glucose. (3) The technique of the '983 patent uses stimulated Raman spectroscopy in which only one specific stimulated Raman line of glucose is measured with a fixed pair of pump and probe wavelengths whereas the technique of the present invention preferably involves obtaining an excitation Raman spectrum using a plurality of pump laser wavelengths. (4) The technique of the '983 patent measures glucose concentration only in the aqueous ocular humor of the eye whereas our technique is not so limited. It can readily be appreciated that the use of laser beams on the eye could be dangerous, especially if their power levels are high. Moreover, the pass length of the Raman signal produced in tissues is much larger than that in the eye by a factor of $z=L^2/l_t$ where L is the sample length and $l_t$ is the scattering length of the tissue.

The discussion below includes examples of the Raman modes for a variety of biological materials.

Figure 4:
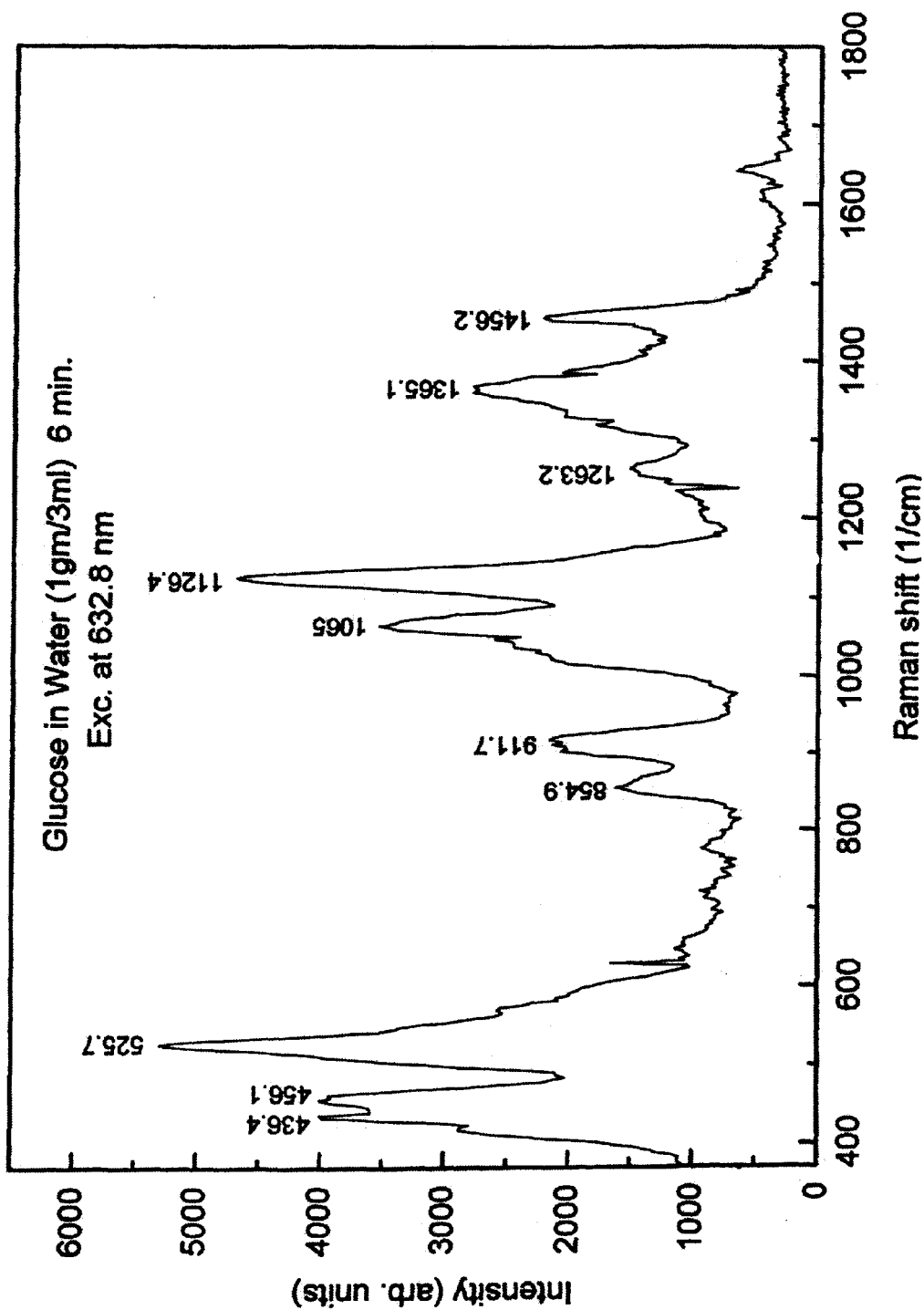
FIG. 4 is a graphic representation of the near-infrared spontaneous Raman spectrum of glucose following excitation at 632.8 nm with a 5 mW He—Ne laser.

Referring now to FIG. 4, there is shown a graph depicting the near-infrared spontaneous Raman spectrum of glucose measured following excitation with a 5 mW He—Ne laser. Eight Raman modes at 436.4, 525.7, 854.9, 911.7, 1065.0, 1126.4, 1365.1 and 1456.2 $cm^{-1}$ were detected and can be considered to be the fingerprint Raman lines of blood glucose. Additional measurements were taken with glucose concentrations varying from 1 g/ml to $10^{-2}$ g/ml, and the results show that the intensities of these Raman lines decrease proportionally with a decrease in the concentration of glucose. This suggests that, in principle, the concentration level of blood glucose can be determined by measuring the Raman spectrum. However, in practice, the concentration of human blood glucose ranges from as low as $\sim 0.7$–$1.1\times10^{-3}$ g/ml for non-diabetic people and $>1.1\times10^{-3}$ g/ml for diabetic people. The spontaneous Raman intensity for such low concentrations of glucose would be too weak to be measured in a reasonable exposure time. In fact, in our experiments, a Raman signal could not be realized when the concentration of glucose decreases below $10^{-2}$ g/ml, even if the exposure time is as long as 20 minutes. The Raman intensity could be increased by increasing the pump power, but a high-power pump is not suitable for in vitro and in vivo diagnostic applications. Consequently, it can be appreciated that conventional spontaneous Raman spectroscopy is hard or even impossible to use to detect physiological concentrations of blood glucose.

Figure 5:
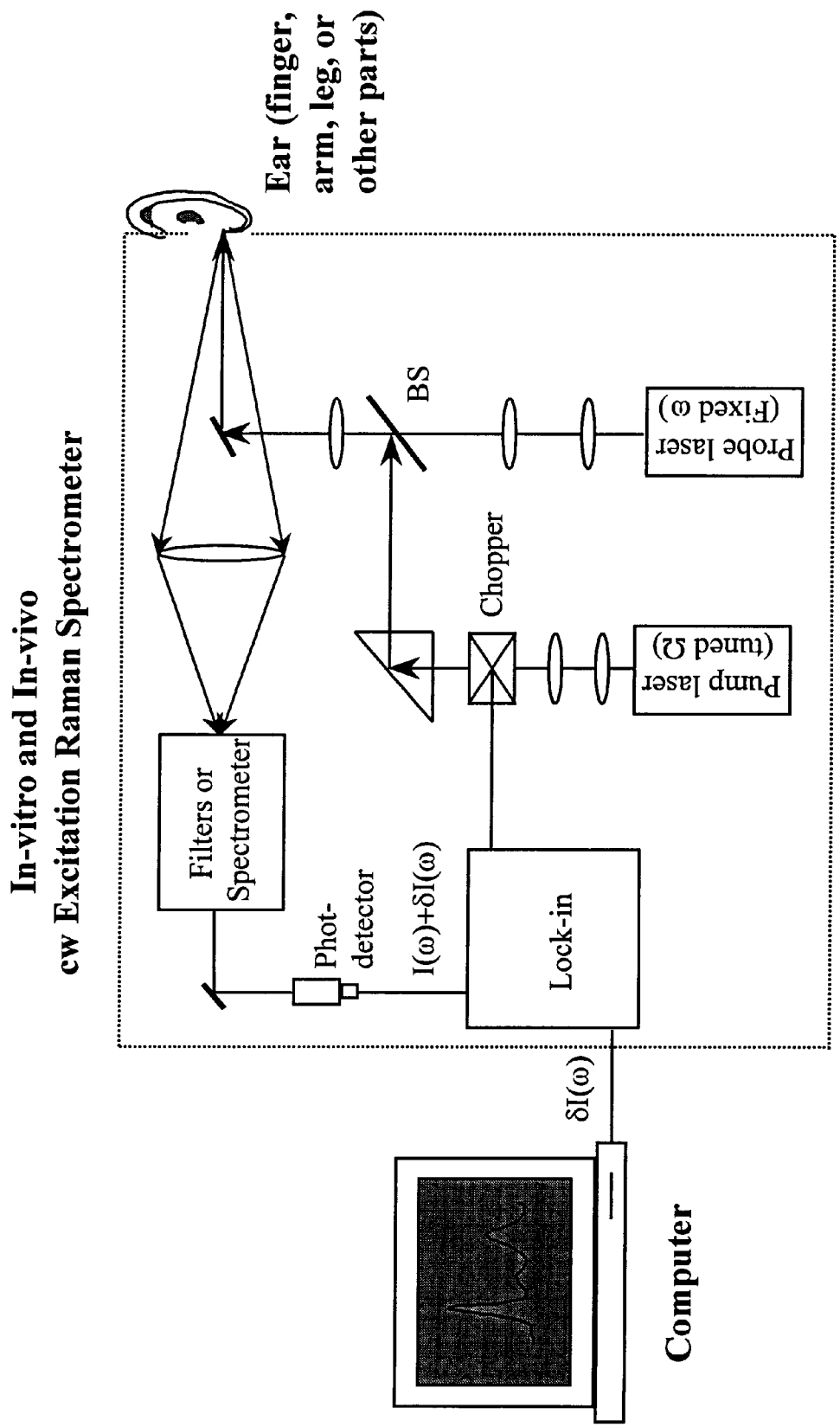
FIG. 5 is a schematic diagram of a second embodiment of a system constructed according to the teachings of the present invention for examining biological materials using low-power cw excitation Raman spectroscopy.

By contrast, the technique of the present invention can be used to detect in vitro and/or in vivo the concentration level of blood glucose by using, for example, a low-power He—Ne laser as the probe and a low-power tunable dye laser as the pump. This could be done by tuning the pump wavelength from 570 nm to 630 nm and then measuring the Raman gain at the probe wavelength of 632.8 nm to reveal the excitation Raman peaks from 436.4 to 1456.2 $cm^{-1}$. The modes of 525.7 and 1126.4 $cm^{-1}$, which have high Raman cross-section and narrow band width, are expected to be enhanced with larger gain factors. The exposure time can be decreased to somewhere in the range of ten seconds. The measured intensities of the excitation Raman peaks can be used to detect concentration levels of the blood glucose, from which measurements diabetes can be diagnosed. (The normal range for fasting blood glucose is 70–110 mg/dl.) Such measurements can be done not only for blood samples but also for body parts in vivo, such as fingers, arms, ears and/or legs. FIG. 5 is a schematic diagram of a system that can be used to measure the fingerprint Raman spectrum for blood glucose present in ears, fingers, arms, legs or other body parts, in vivo, using the cw excitation Raman spectroscopic method of the present invention. As can readily be appreciated, the system of FIG. 5 represents a substantial improvement over existing blood glucose monitoring techniques which require the drawing of a blood sample from a patient.

Figure 6:
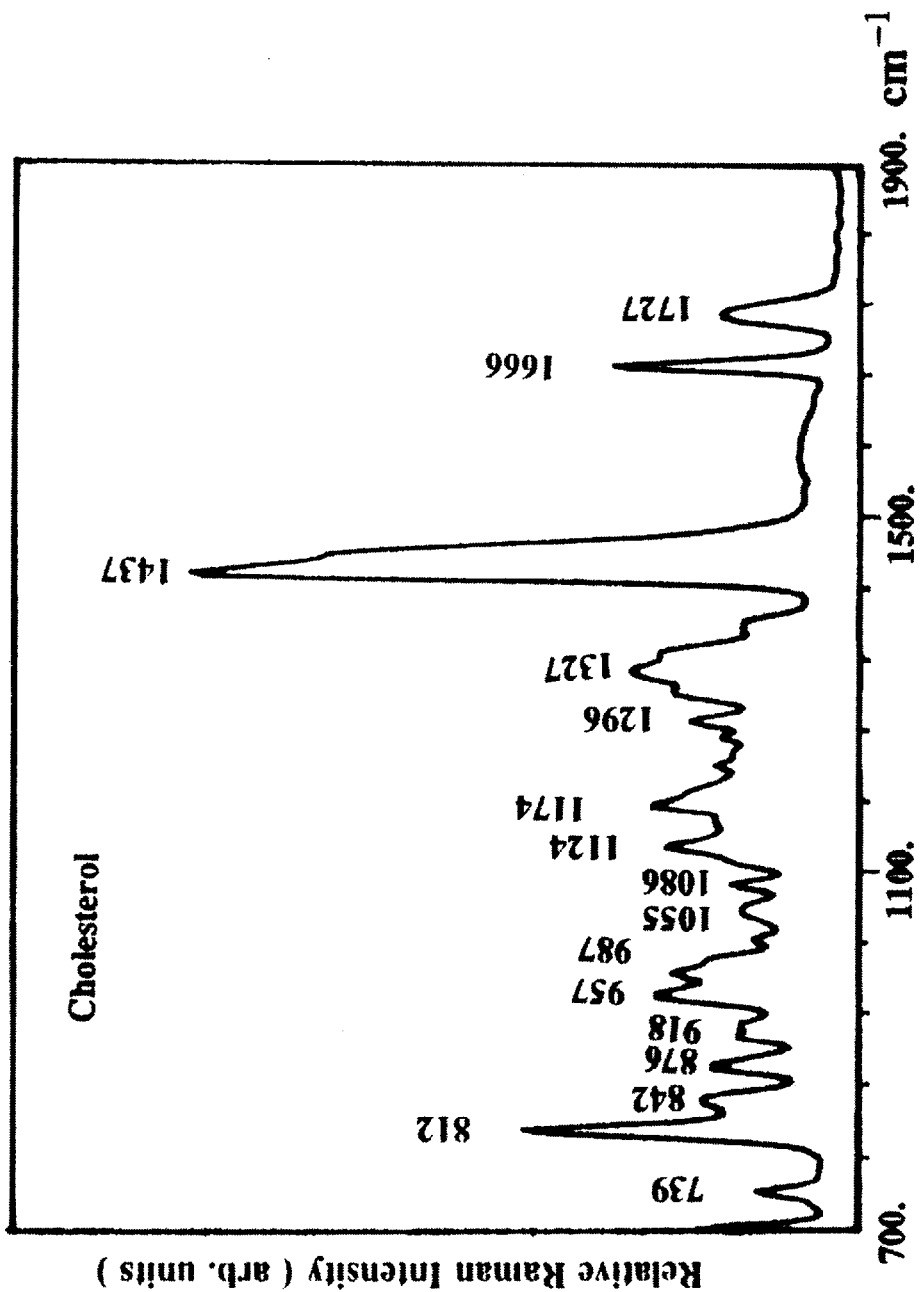
FIG. 6 is a graphic representation of the Raman spectrum of blood cholesterol following excitation at 1.064 $\mu$m with a 1 W Nd:YAG laser.

FIG. 6 is a graph depicting the spontaneous Raman spectrum of blood cholesterol obtained following excitation with a 1.064 μm Nd:YAG laser pump at 1 W power. The Raman modes of 812, 1437, 1666 and 1727 cm$^{-1}$ are the fingerprint Raman lines for blood cholesterol. The low-power cw excitation Raman spectroscopy technique of the present invention can be used to measure these modes using low-power laser sources and short exposure times. The measured intensities of the excitation Raman lines of cholesterol can be used to detect its concentration level in a blood sample and, hence, to be used in the diagnosis of heart disease. (The normal range of blood choleterol depends upon a person's age and sex. Under the age of 40—less than 190 mg/dl is considered normal. Over the age of 40—up to 250 mg/dl is considered normal.) As noted above, the technique of the present invention can also be used to detect the concentration levels of other Raman-active constituents in blood, such as SGOT/SGPT for hepatitis detection (normal range: 0–50 mg/dl), blood urea nitrogen (BUN) and creatinine for kidney function (normal ranges: 10–20 mg/dl for BUN and 0.5–1.5 for creatinine), acid phosphatase for prostate cancer detection (normal range: 0–2 U/L), sodium, potassium, chloride, uric acid, albumin and globulin. The present technique can also be used to detect the levels of Raman-active constituents in urine, lymph and saliva.

Figure 7:
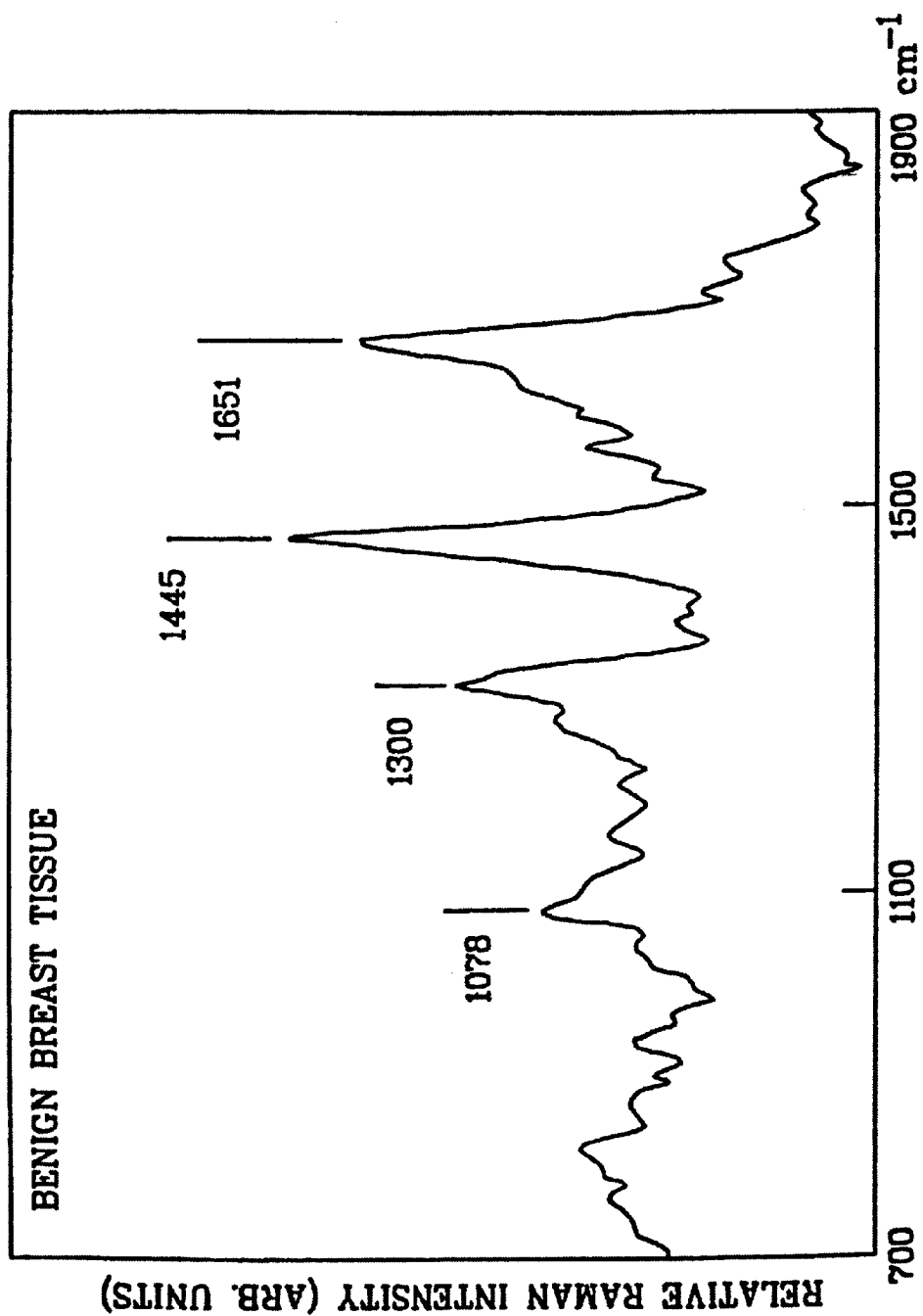
FIG. 7 is a graphic representation of the Raman spectrum of normal or benign human breast tissue following Nd:YAG laser excitation with 1 W power and a pulse duration of ~20 ps.
Figure 8:
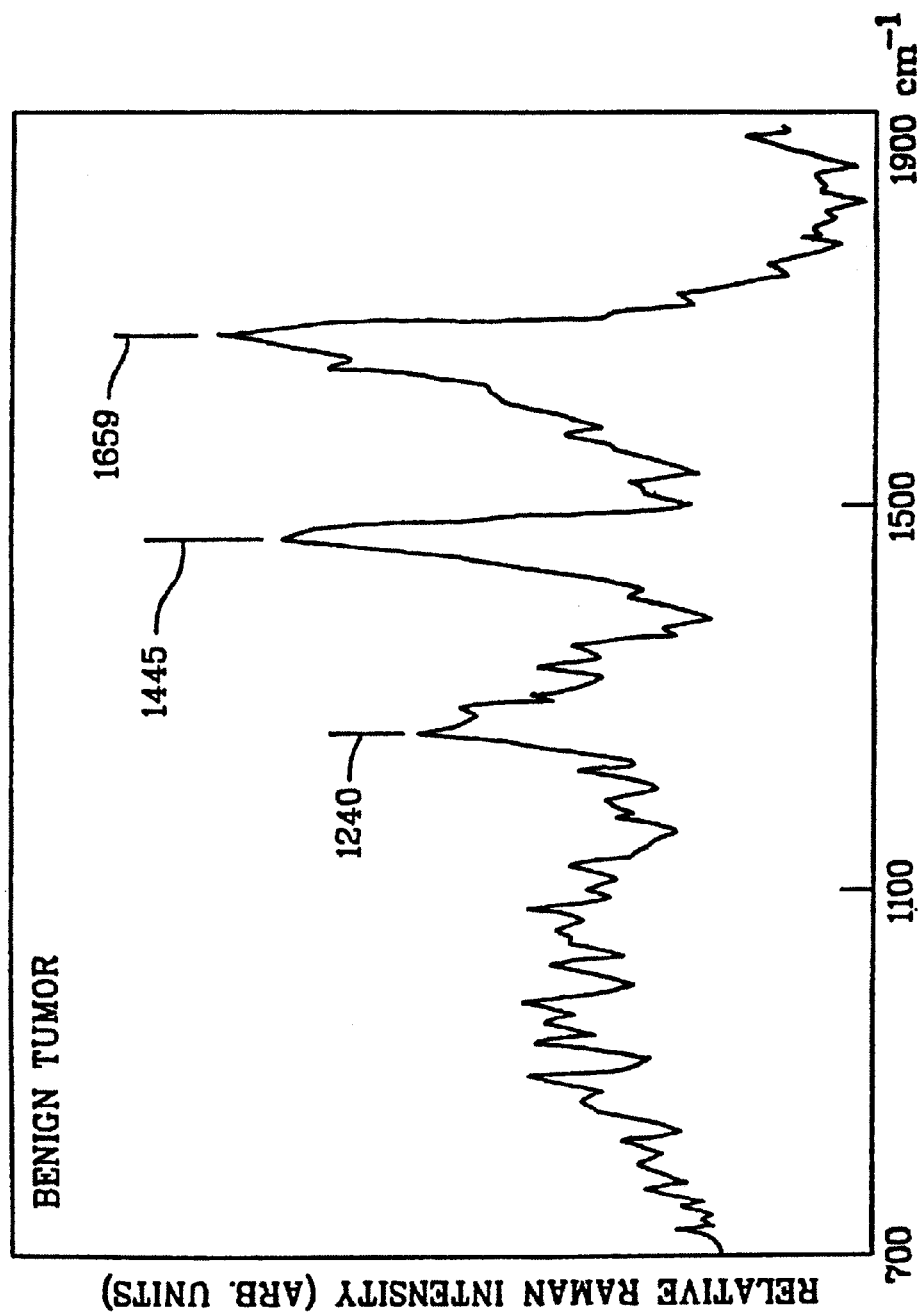
FIG. 8 is a graphic representation of the Raman spectrum of benign tumor human breast tissue following Nd:YAG laser excitation with 1 W power and a pulse duration of ~20 ps.
Figure 9:
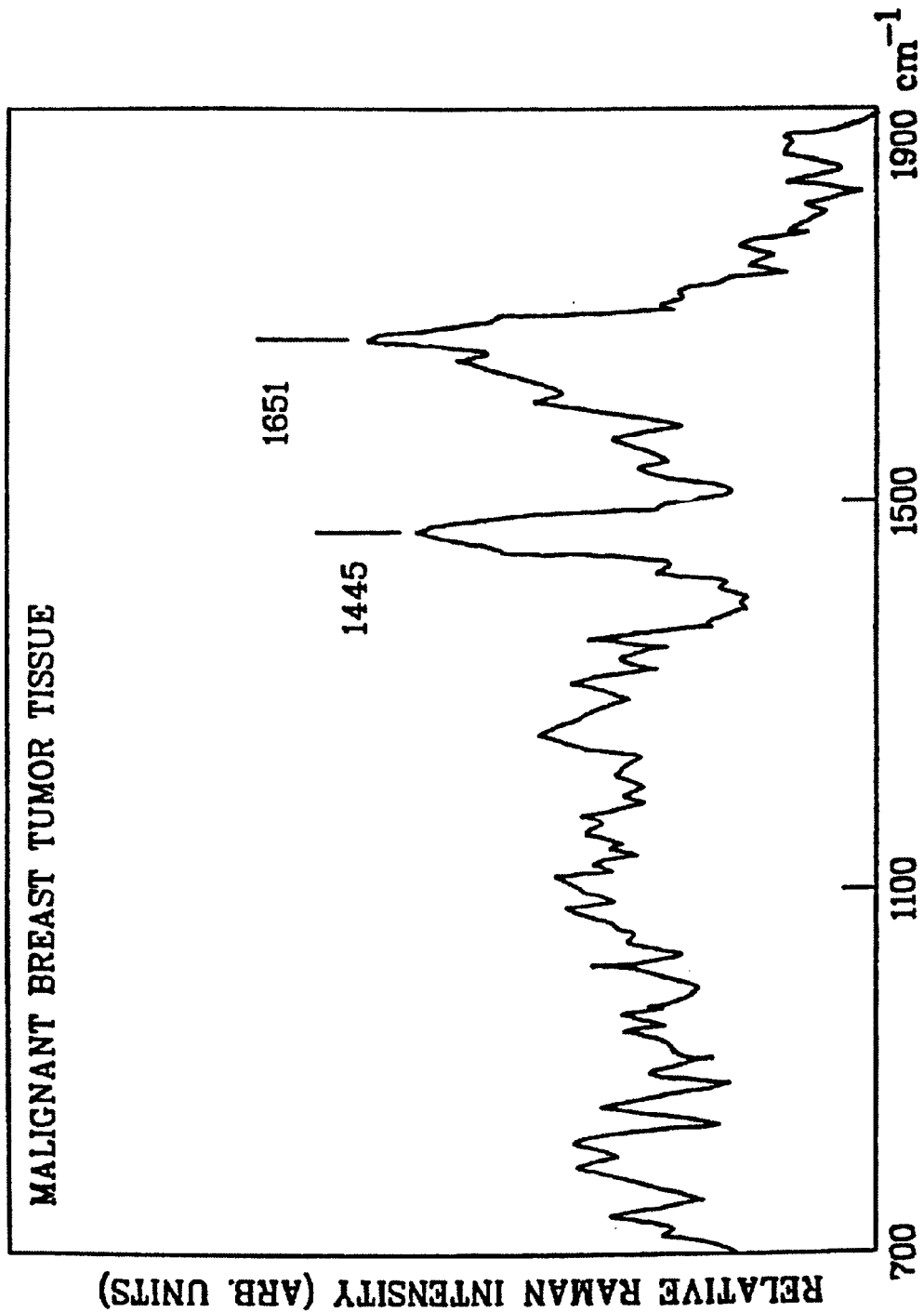
FIG. 9 is a graphic representation of the Raman spectrum of malignant tumor human breast tissue following Nd:YAG laser excitation with 1 W power and a pulse duration of ~20 ps.

Referring now to FIGS. 7 through 9, there are shown graphs depicting the spontaneous Raman spectra of normal or benign human breast tissue, benign tumor human breast tissue and malignant tumor human breast tissue, respectively, following Nd:YAG laser excitation with 1 W power and a pulse duration of ~20 ps. The fingerprint Raman modes are 1078, 1300, 1445 and 1651 cm$^{-1}$ for normal and benign breast tissues, 1240, 1445 and 1659 cm$^{-1}$ for benign tumor tissues and 1445 and 1651 cm$^{-1}$ for malignant tumor tissues. Whereas the spectra of FIGS. 7 through 9 were obtained using a Nd:YAG laser at 1 W power, this type of laser could not be used for in vivo and in vitro examinations because it is far above the safety limitations for human bodies. A pair of low-power lasers could be used, however, if one were to employ the technique of the present invention. For example, a low-power He—Ne laser or a semiconductor diode laser could be used as the probe and a tunable dye laser or a Ti:Sapphire laser could be used as the pump in the present technique. By tuning the pump wavelength and measuring the excitation Raman gain at the probe wavelength, the positions of the excitation Raman peaks can be used for tumor detection according to the known fingerprint Raman spectra for normal, benign tumor and malignant tumor tissues mentioned above.

Figure 10:
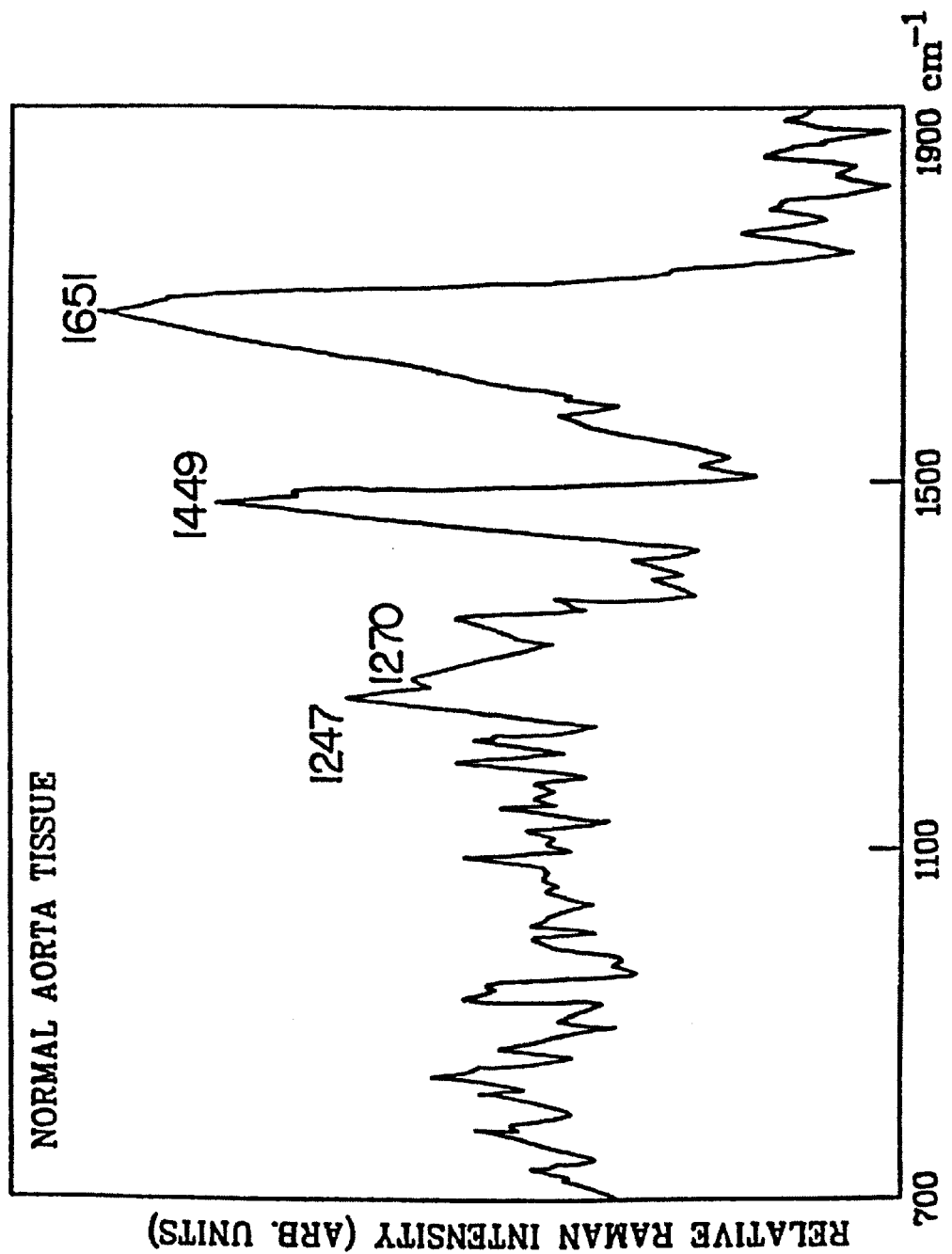
FIG. 10 is a graphic representation of the Raman spectrum of normal aortic tissue following Nd:YAG laser excitation with 1 W power.
Figure 11:
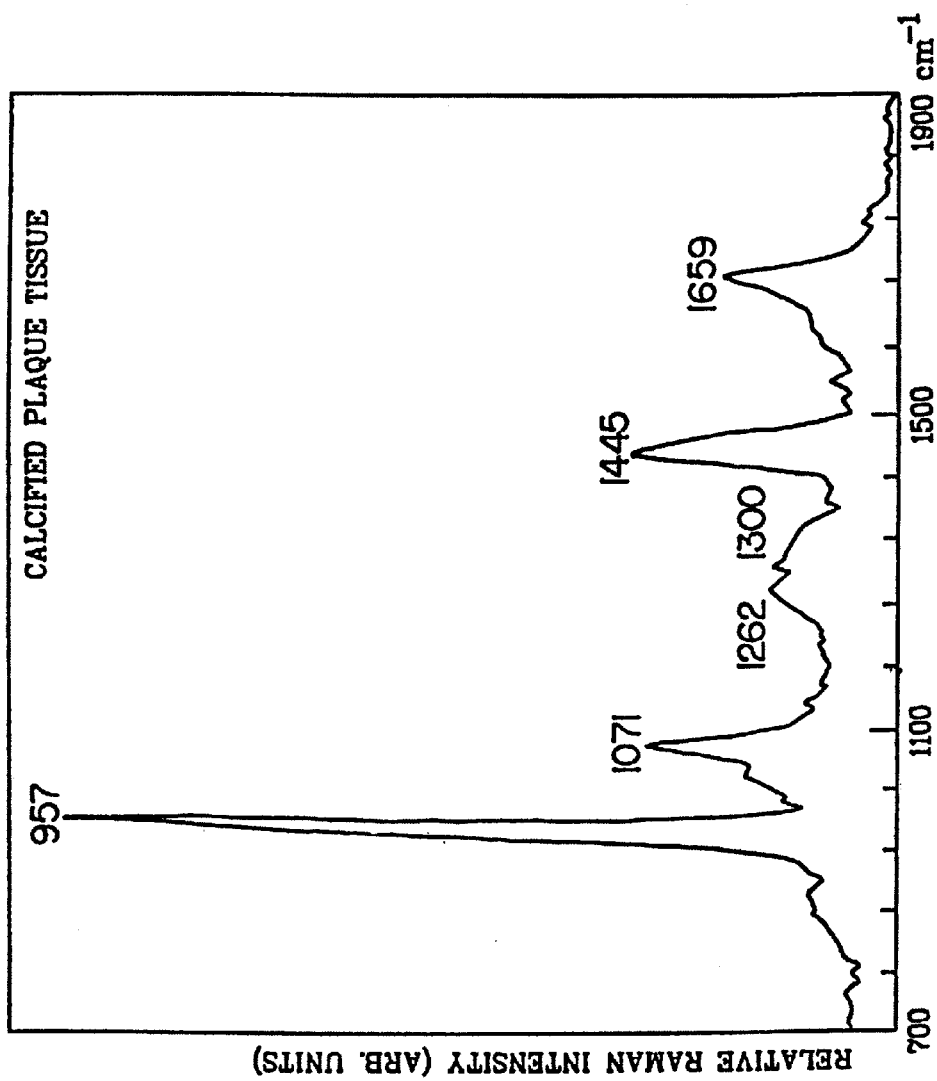
FIG. 11 is a graphic representation of the Raman spectrum of calcified plaque tissue following Nd:YAG laser excitation with 1 W power.
Figure 12:
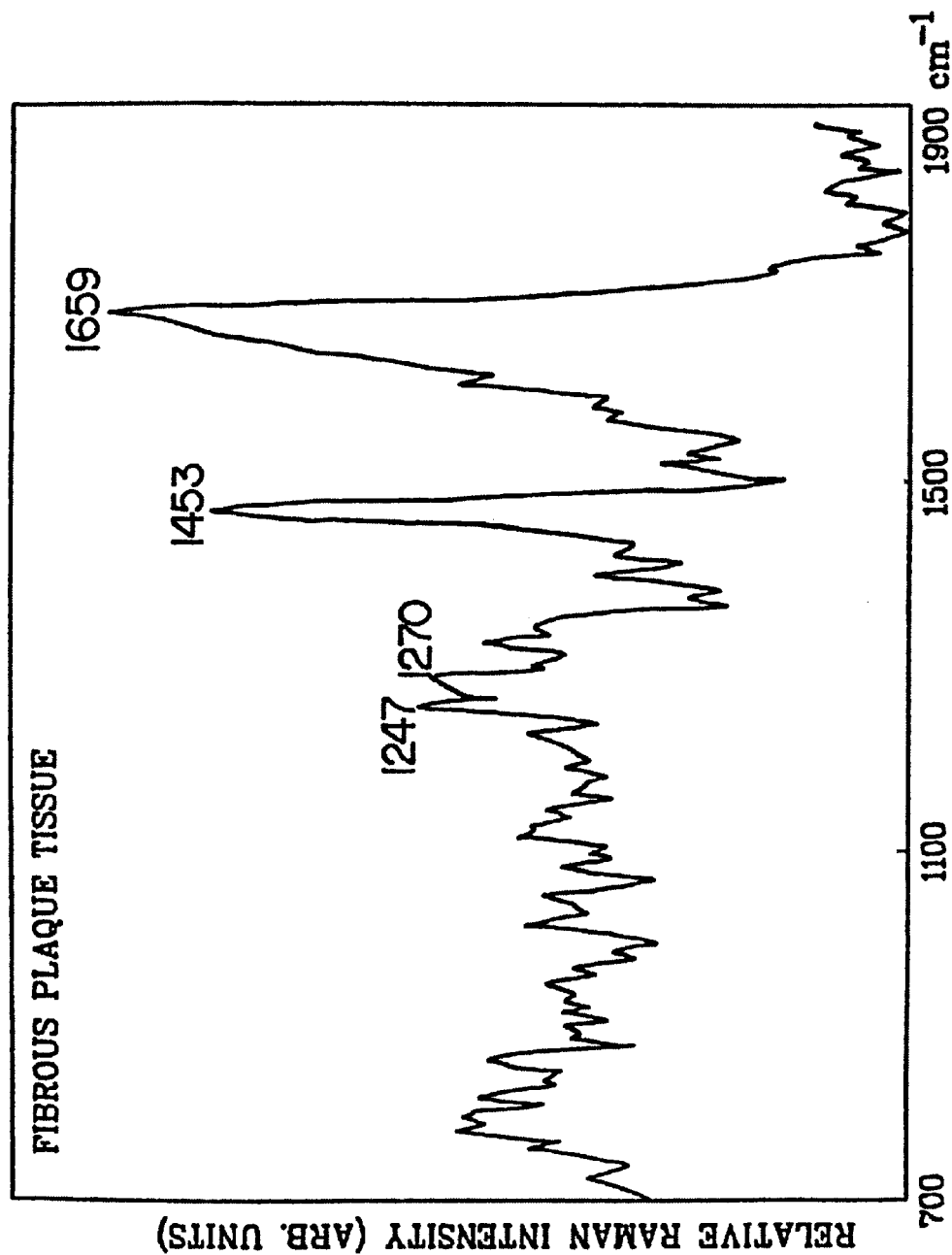
FIG. 12 is a graphic representation of the Raman spectrum of fibrous plaque tissue following Nd:YAG laser excitation with 1 W power.

Referring now to FIGS. 10 through 12, there are shown graphs depicting the spontaneous Raman spectra of normal aortic tissue, calcified plaque tissue and fibrous plaque tissue, respectively. The fingerprint Raman modes are 1247, 1270, 1449 and 1651 cm$^{-1}$ for normal aortic tissue, 957, 1071, 1445 and 1659 cm$^{-1}$ for calcified plaque tissue and 1247, 1270, 1453 and 1659 cm$^{-1}$ for fibrous plaque tissue.

Figure 13A:
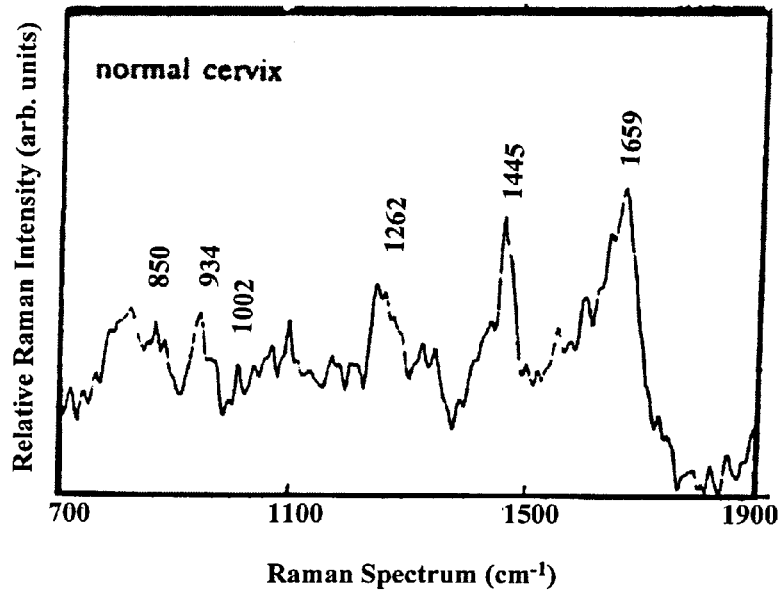
FIGS. 13(a) through 13(c) are graphic representations of the Raman spectra of normal, benign and cancerous cervical tissues, respectively.
Figure 13B:
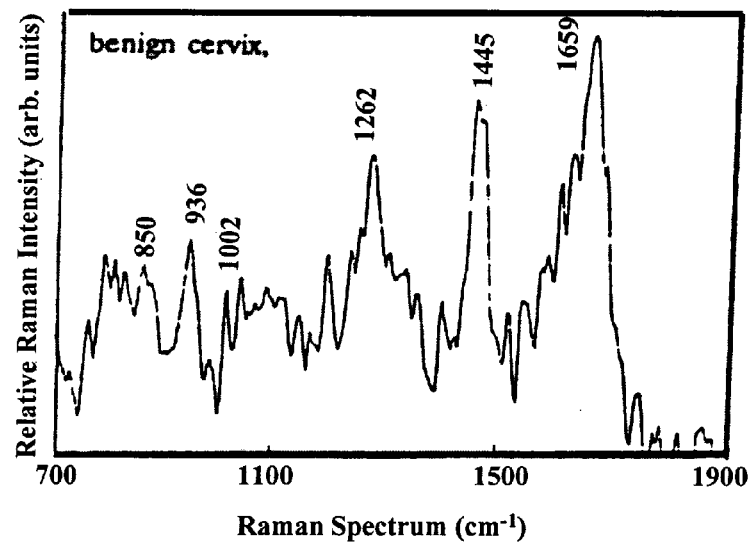
Figure 13C:
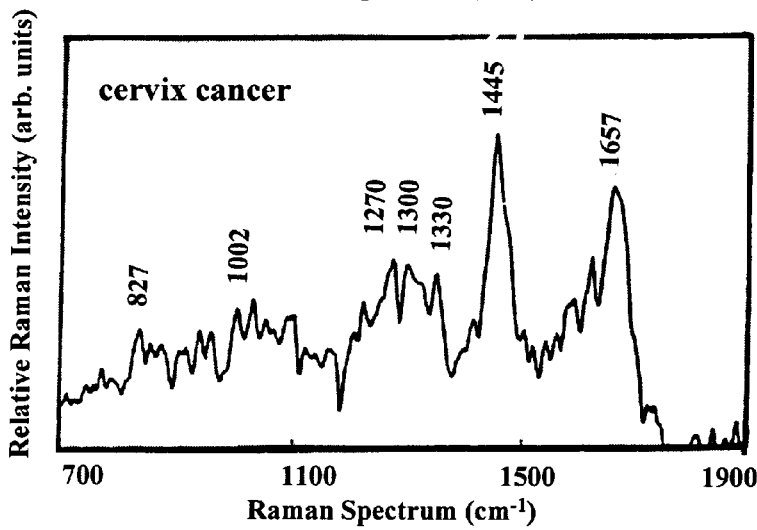

Referring now to FIGS. 13(a) through 13(c), there are shown graphs depicting the spontaneous Raman spectra of normal, benign and cancerous cervical tissues, respectively. The fingerprint Raman modes are 1270, 1445 and 1657 cm$^{-1}$ for cancerous cervical tissues and 934, 1262, 1445 and 1659 cm$^{-1}$ for normal and benign cervical tissues. In addition, the relative intensities of different Raman lines for the cancerous cervical tissue are different from that of the normal and benign cervical tissues.

Figure 14A:
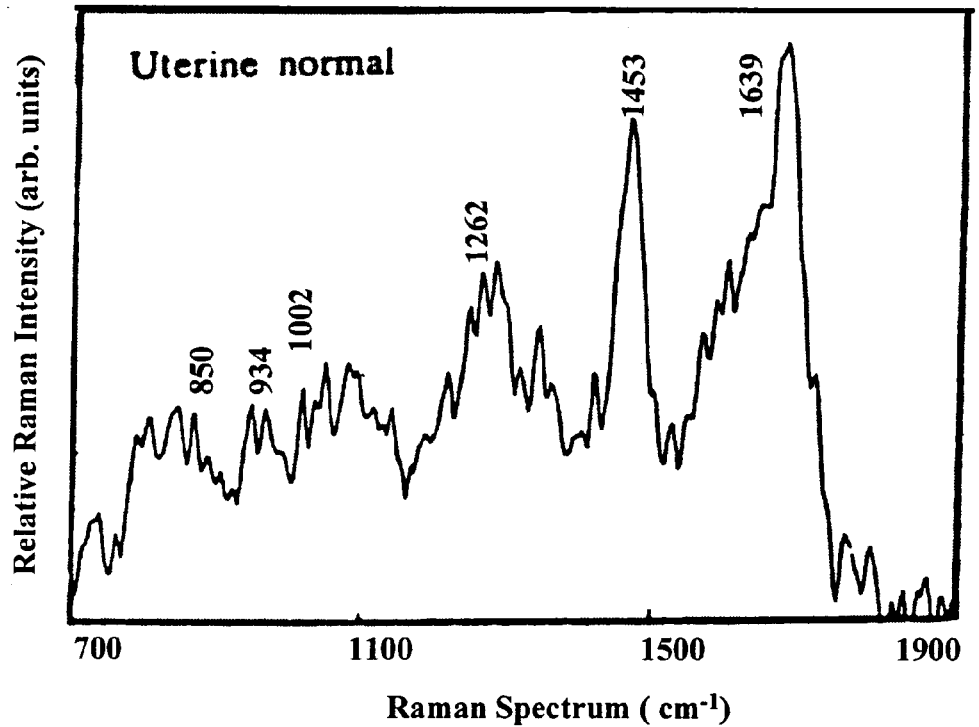
FIGS. 14(a) and 14(b) are graphic representations of the Raman spectra of normal and cancerous uterine tissues, respectively.
Figure 14B:
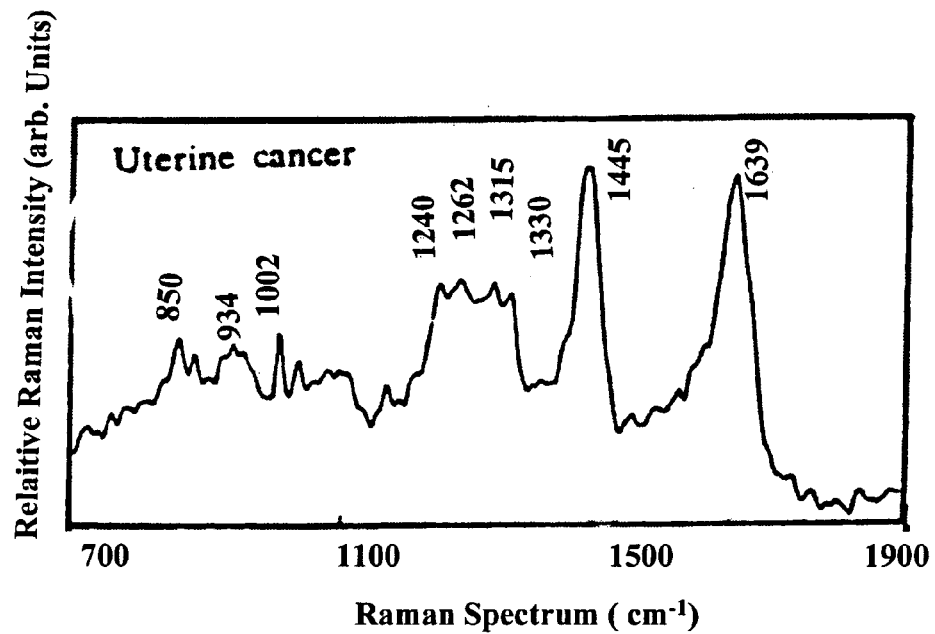

Referring now to FIGS. 14(a) and 14(b), there are shown the spontaneous Raman spectra of normal and cancerous uterine tissues, respectively. Two Raman peaks at 1445 and 1659 cm$^{-1}$ and one broad band in the region of 1240–1330 cm$^{-1}$ are present for the cancerous uterine tissue with a relative intensity of $I_{1659} < I_{1445}$. Three characteristic Raman lines are observed at 1262, 1453 and 1659 cm$^{-1}$ for the normal uterine tissue with a relative intensity of $I_{1659} > I_{1453} > I_{1262}$.

Figure 15A:
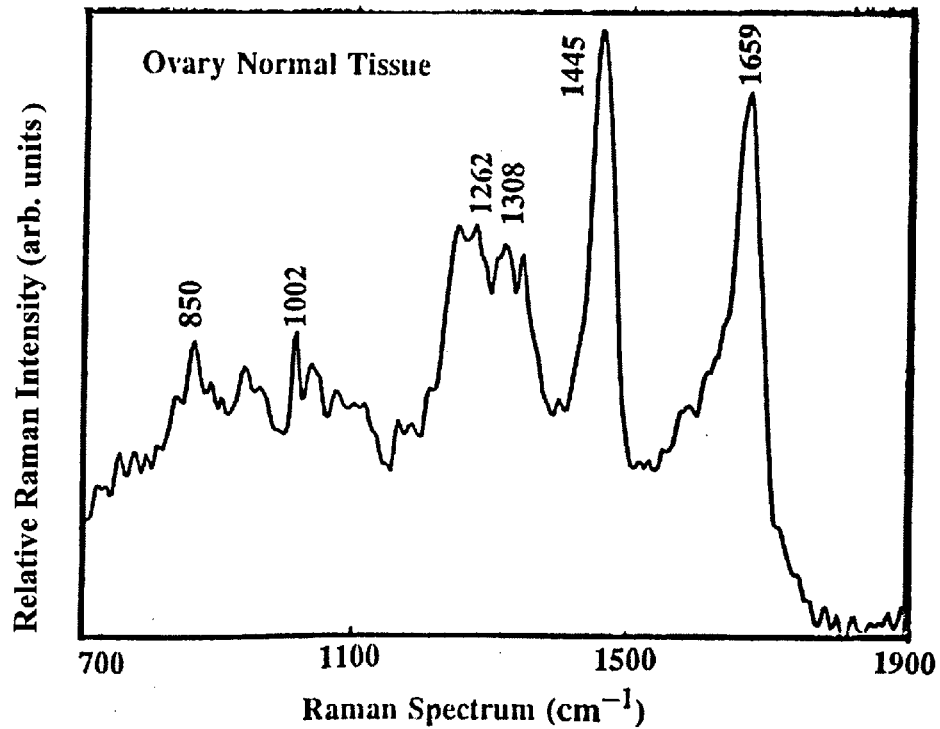
FIGS. 15(a) and 15(b) are graphic representations of the Raman spectra of normal and cancerous ovarian tissues, respectively.
Figure 15:
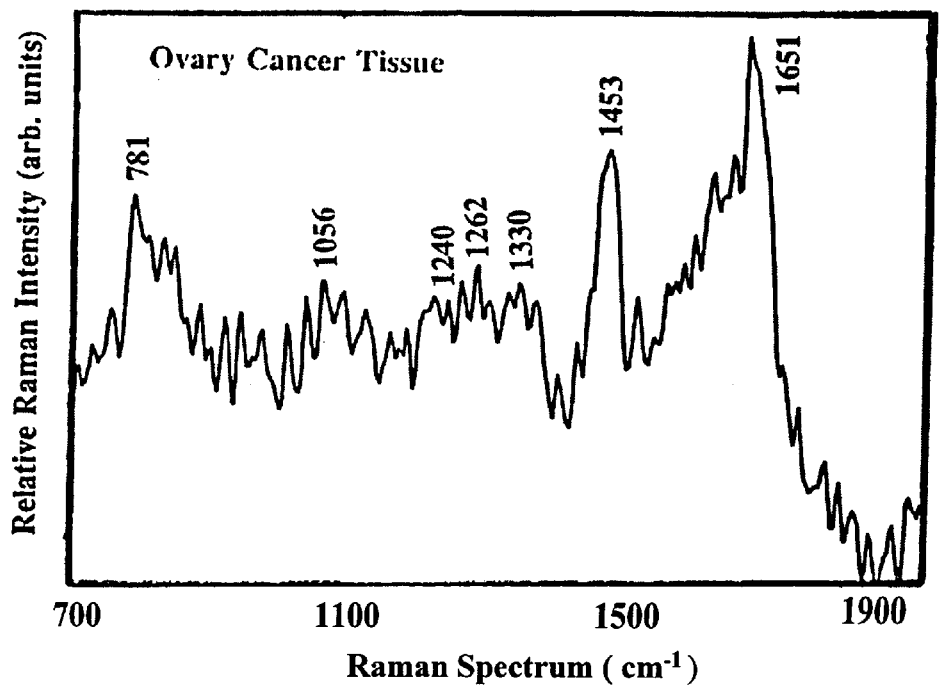

Referring now to FIGS. 15(a) and 15(b), there are shown the spontaneous Raman spectra of normal and cancerous ovarian tissues, respectively. Two Raman peaks at 1453 and 1651 cm$^{-1}$ are present for cancerous ovarian tissue with a relative intensity of $I_{651} > I_{1453}$. Two characteristic Raman lines at 1445 and 1659 cm$^{-1}$ and a band region at 1262–1308 cm$^{-1}$ are present for normal ovarian tissue with a relative intensity of $I_{1659} < I_{1445}$.

Referring now to FIG. 16, there is shown a schematic diagram of a low-power cw excitation Raman spectroscopic system that can be used to measure, in vivo and/or in vitro, the characteristic Raman spectra of various tissues and other biological materials of a patient. As can be seen, the system includes an optical fiber bundle probe that can be inserted into a patient for examining various internal organs.

The technique of the present invention can additionally be used to detect a disease state in an organ, such as the brain, throat, esophagus, stomach, intestines, lung, liver, kidney, prostate, pancreas and bladder. In addition, the present technique can also be used for early tumor or cancer detection by measuring the level of nitric oxide in a sample (nitric oxide concentration being an indicator of cancer) using the fingerprint Raman mode of 1877±2 cm$^{-1}$ for nitric oxide.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of examining an object, said method comprising the steps of:

(a) irradiating the object with a first pump beam at a first wavelength, whereby the object produces a spontaneous Raman emission at a second wavelength;

(b) substantially simultaneously with step (a), irradiating the object with a first probe beam at a third wavelength, whereby the intensity of said first probe beam emitted from the object at said third wavelength increases if said third wavelength is equal to said second wavelength;

(c) detecting the intensity of said first probe beam emitted from the object at said third wavelength following steps (a) and (b), whereby an increase in intensity of said first probe beam at said third wavelength indicates the presence of a Raman mode for the object at said first wavelength;

(d) irradiating the object with a second pump beam at a fourth wavelength, whereby the object produces a spontaneous Raman emission at a fifth wavelength, said fourth wavelength not being equal to said first wavelength;

(e) substantially simultaneously with step (d), irradiating the object with said first probe beam at said third wavelength, whereby the intensity of said first probe beam emitted from the object at said third wavelength increases if said third wavelength is equal to said fifth wavelength; and (f) detecting the intensity of said first probe beam emitted from the object at said third wavelength following steps (d) and (e), whereby an increase in intensity of said first probe beam at said third wavelength indicates the presence of a Raman mode for the object at said fourth wavelength.

2. The method as claimed in claim 1 further comprising the steps of:

(g) irradiating the object with a pump beam at a wavelength other than said first wavelength and said fourth wavelength;

(h) substantially simultaneously with step (g), irradiating the object with said first probe beam at said third wavelength;

(i) detecting the intensity of said first probe beam emitted from the object at said third wavelength following steps (g) and (h);

(j) repeating steps (g) through (i) until a spectrum of different pump beam wavelengths have been used; and (k) generating an excitation Raman spectrum for the object using the intensities detected in steps (c), (f) and (i).

3. The method as claimed in claim 2 wherein the object is a biological material.

4. The method as claimed in claim 2 wherein the object is a blood sample.

5. The method as claimed in claim 4 further comprising the step of comparing the detected intensities at one or more of the Raman modes for blood glucose to appropriate standards so that the concentration of blood glucose in the blood sample can be determined.

6. The method as claimed in claim 4 further comprising the step of comparing the detected intensities at one or more of the Raman modes for serum cholesterol to appropriate standards so that the concentration of serum cholesterol in the blood sample can be determined.

7. The method as claimed in claim 4 further comprising the step of comparing the detected intensities at one or more of the Raman modes for serum glutamic oxalacetic transaminase and serum glutamic pyruvic transaminase to appropriate standards so that the concentrations of serum glutamic oxalacetic transaminase and serum glutamic pyruvic transaminase in the blood sample can be determined.

8. The method as claimed in claim 4 further comprising the step of comparing the detected intensities at one or more of the Raman modes for blood urea nitrogen to appropriate standards so that the concentration of blood urea nitrogen in the blood sample can be determined.

9. The method as claimed in claim 4 further comprising the step of comparing the detected intensities at one or more of the Raman modes for creatinine to appropriate standards so that the concentration of creatinine in the blood sample can be determined.

10. The method as claimed in claim 4 further comprising the step of comparing the detected intensities at one or more of the Raman modes for acid phosphatase to appropriate standards so that the concentration of acid phosphatase in the blood sample can be determined.

11. The method as claimed in claim 3 wherein the biological material is a tissue sample, said method further comprising the step of comparing said excitation Raman spectrum to appropriate standards obtained for cancerous and noncancerous tissues of the same type.

12. The method as claimed in claim 11 wherein the tissue sample is a human breast tissue sample.

13. The method as claimed in claim 11 wherein the tissue sample is a human cervical tissue sample.

14. The method as claimed in claim 11 wherein the tissue sample is a human uterine tissue sample.

15. The method as claimed in claim 11 wherein the tissue sample is a human ovarian tissue sample.

16. The method as claimed in claim 3 wherein the biological material is a urine, lymph, saliva, semen or tear sample.

17. The method as claimed in claim 3 wherein the biological material is a human aortic tissue sample, said method further comprising the step of comparing said excitation Raman spectrum to appropriate standards obtained for normal human aortic tissue, calcified human plaque tissue and fibrous human plaque tissue.

18. The method as claimed in claim 1 wherein the object examined is part of a living being and wherein said method is performed in vivo.

19. The method as claimed in claim 1 further comprising the step of comparing the intensities detected in steps (c) and (f) to the intensity of said first probe beam emitted from the object at said third wavelength in the absence of a pump beam.

20. The method as claimed in claim 1 wherein one of said first and said fourth wavelengths is a known Raman mode for the object being examined and wherein the other of said first and said fourth wavelengths is known not to be a Raman mode for the object being examined.

21. A system for examining an object, said system comprising:

(a) means for producing a first low-power pump beam at a first wavelength;

(b) means for producing a second low-power pump beam at a second wavelength, said second wavelength differing from said first wavelength;

(c) means for producing a first low-power probe beam at a third wavelength, said third wavelength differing from each of said first and second wavelengths;

(d) optics for combining said first low-power probe beam and said first low-power pump beam into a first combined beam focused on the object and for combining said first low-power probe beam and said second low-power pump beam into a second combined beam focused on the object; and (e) means for detecting the intensity of light emitted from the object at said third wavelength.

22. The method as claimed in claim 21 further comprising a chopper for modulating said first and second low-power pump beams prior to their combination with said first low-power probe beam and further comprising a lock-in amplifier for demodulating the light emitted from the object at said third wavelength and detected by said detecting means.

\* \* \* \* \*